(12) United States Patent
Akahoshi

(10) Patent No.: US 9,889,247 B2
(45) Date of Patent: Feb. 13, 2018

(54) INFUSION SLEEVE WITH DISTENDABLE PORT

(71) Applicant: Art, Limited, Grand Cayman (KY)

(72) Inventor: Takayuki Akahoshi, Toyko (JP)

(73) Assignee: Art, Limited (KY)

( * ) Notice: Subject to any disclaimer, the term of this patent is extended or adjusted under 35 U.S.C. 154(b) by 204 days.

(21) Appl. No.: 14/315,549

(22) Filed: Jun. 26, 2014

(65) Prior Publication Data

US 2014/0309650 A1    Oct. 16, 2014

Related U.S. Application Data

(63) Continuation-in-part of application No. 12/856,358, filed on Aug. 13, 2010, now Pat. No. 8,864,710.

(60) Provisional application No. 61/293,399, filed on Jan. 8, 2010, provisional application No. 61/293,389, filed on Jan. 8, 2010.

(51) Int. Cl.
*A61M 3/02* (2006.01)
*A61F 9/007* (2006.01)
*A61M 1/00* (2006.01)
*A61B 17/32* (2006.01)

(52) U.S. Cl.
CPC ....... *A61M 3/0279* (2013.01); *A61F 9/00745* (2013.01); *A61M 1/0084* (2013.01); *A61B 2017/320084* (2013.01)

(58) Field of Classification Search
CPC ............. A61M 3/0279; A61M 1/0084; A61F 9/00745; A61B 17/320084
See application file for complete search history.

(56) References Cited

U.S. PATENT DOCUMENTS

| | | | | |
|---|---|---|---|---|
| 5,188,589 A * | 2/1993 | Wypych | ............. | A61F 9/00745 604/22 |
| 5,725,495 A * | 3/1998 | Strukel | ............... | A61M 1/0035 604/22 |
| 6,293,958 B1 * | 9/2001 | Berry | ................ | A61M 25/0075 604/264 |
| 7,491,192 B2 * | 2/2009 | DiFiore | ............. | A61M 25/0075 604/236 |

* cited by examiner

*Primary Examiner* — Bradley Osinski
(74) *Attorney, Agent, or Firm* — Wood, Phillips, Katz, Clark & Mortimer

(57) ABSTRACT

A phacoemulsification irrigation sleeve having a body configured to operatively connect to a phacoemulsification needle. The body has proximal and distal ends and defines a passageway for liquid. A first irrigation port is formed in the body between its proximal and distal ends. The body is slit to define a first flap configured to swing away from the first irrigation port in response to pressure of fluid flowing in the passageway to thereby reduce resistance of fluid flow through the first irrigation port. The first flap, when swung away from the first irrigation port, is oriented to direct fluid flowing through the first irrigation port in a direction from the proximal end of the body toward the distal end of the body.

16 Claims, 5 Drawing Sheets

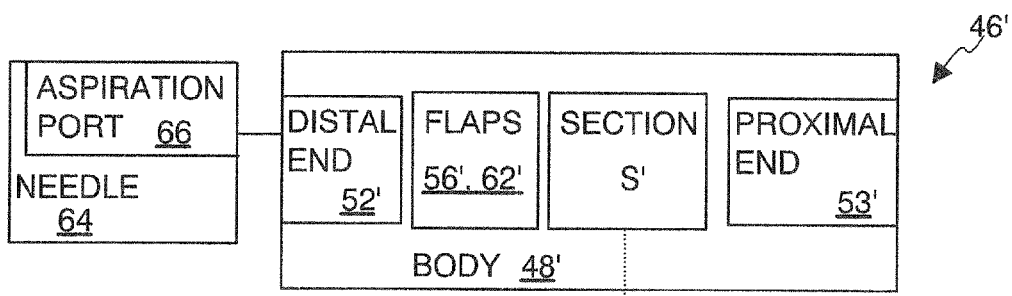
Fig. 13
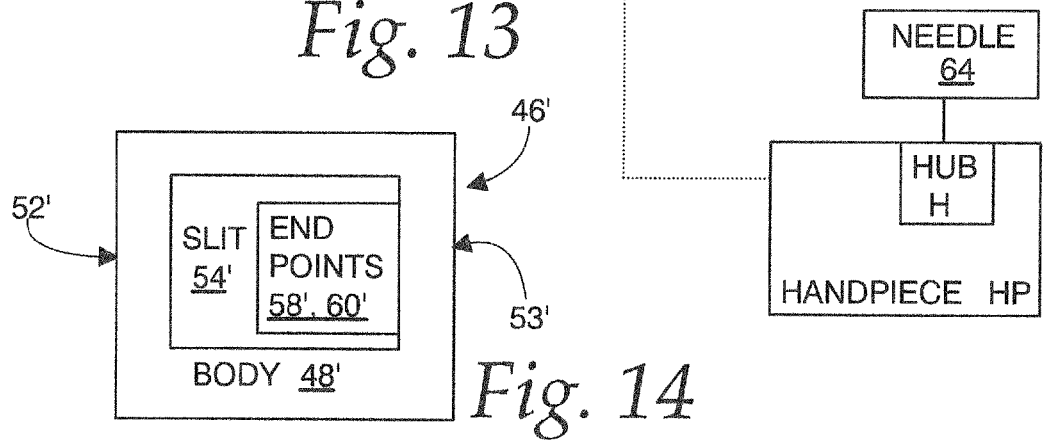
Fig. 14
Fig. 16
Fig. 15
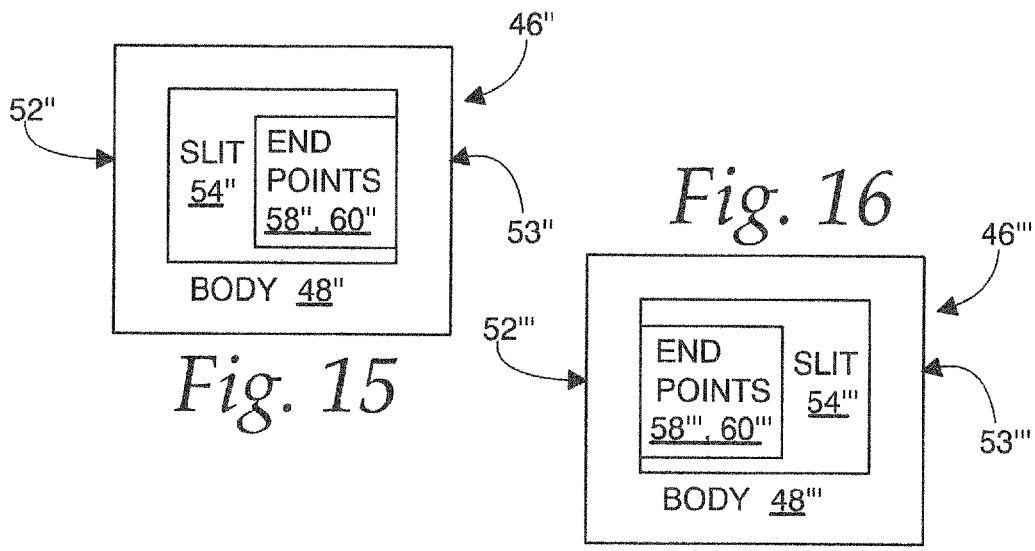
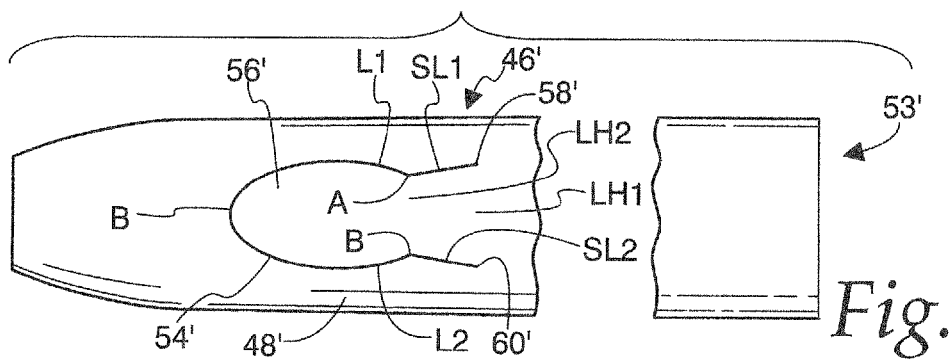
Fig. 17

INFUSION SLEEVE WITH DISTENDABLE PORT

CROSS-REFERENCE TO RELATED APPLICATIONS

This application is a continuation-in-part of U.S. patent application Ser. No. 12/856,358, filed Aug. 13, 2010.

BACKGROUND OF THE INVENTION

Field of the Invention

This invention relates to surgical instruments and surgical techniques used in eye surgery and, more particularly, to the technique of phacoemulsification apparatus and methods for their use.

Background Art

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such technique is known as phacoemulsification. A typical phacoemulsification tool includes a hollow needle to which electrical energy is applied to vibrate the needle at ultrasonic frequencies in order to fragment the diseased lens into small enough particles to be aspirated from the eye. Commonly, an infusion sleeve is mounted around the needle to supply irrigating liquids to the eye in order to aid in flushing and aspirating the lens particles and cortical material through an aspiration port formed in the hollow needle.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such a collapse and this damage is permanent because these cells do not regenerate. One of the benefits of using as small an incision as possible during such surgery is the minimization of leakage during and after surgery which aids in the prevention of such a collapse.

One way to ensure infusion of a sufficient amount of liquid into the eye during an operation is to regulate the flow of irrigating liquid through the sleeve. For example, during phacoemulsification the aspiration port on the phaco needle can become occluded with lens fragments or particles. If the sleeve is of the type having an infusion port at its tip, surrounding the needle, it may also become occluded. When this happens, flow of irrigating liquid into the eye may decrease, meaning that not enough liquid flow may be available to help clear the occlusion. If the surgeon acts to increase liquid flow through the infusion sleeve, this can cause an increase in the Reynolds number of the infusion liquid to the point where the liquid flow becomes turbulent, which can in itself cause damage to the eye.

Flow control may also be desirable, for sleeves having discharge ports that direct the liquid toward the needle tip may create a flow pattern that pushes lens or cortical material away from the aspiration port of the needle, prolonging the phaco procedure.

Instruments using various types of infusing sleeves are well known and well-represented in the art and exemplify the attempts made by others to address the problem of maintaining an adequate flow of irrigating liquid without causing damage to the eye.

U.S. Pat. No. 4,643,717 (Cook et al.) teaches and describes an aspiration fitting adapter formed as a sleeve concentric to the phaco needle and having a pair of bilaterally opposed discharge ports formed proximate the end of the sleeve to infuse irrigating liquid into the eye.

U.S. Pat. No. 5,151,084 (Khek) teaches and describes an ultrasonic needle with an infusion sleeve that includes a baffle. The sleeve of Khek also fits concentrically about the needle and allows the needle to protrude a substantial distance therefrom while providing a pair of discharge ports bilaterally opposed to each other near the terminus of the sleeve.

U.S. Pat. No. 6,117,151 (Ulrich et al.) teaches and describes an eye incision temperature protection sleeve fitted concentrically about a needle and having a single discharge port through which irrigating liquid is passed.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

A series of patents issued to Richard J. Mackool illustrates further variations of irrigating sleeves. Mackool forms the sleeve with a somewhat flattened cross-section configuration intended to more closely approximate the shape of the incision through which the sleeve is inserted into the eye. This cross-section can be seen at FIG. 3 of U.S. Pat. No. 5,084,009.

U.S. Pat. No. 5,084,009 (Mackool) teaches and describes a liquid infusion sleeve for use during eye surgery with the sleeve having a flattened cross-section and having a pair of infusion ports formed on the forward portion of the flattened section.

U.S. Pat. No. 5,286,256 (Mackool) teaches and describes a liquid infusion sleeve having a free-floating rigid sleeve surrounding a needle which is intended to prevent the outer flexible sleeve from collapsing onto the needle.

U.S. Pat. No. 5,354,265 (Mackool) teaches and describes a liquid infusion sleeve showing yet another construction intended to keep the outer flexible infusion sleeve from collapsing onto the vibrating needle.

U.S. Pat. No. 5,505,693 (Mackool) teaches and describes a method and apparatus for reducing friction and heat generation by an ultrasonic device during surgery incorporating a needle support to prevent collapse of the outer flexible sleeve.

The Mackool patents are characterized by a pair of discharge ports formed at the distal end of the sleeve through which irrigating liquid is passed into the eye during the operation.

U.S. Pat. No. 5,645,530 (Boukhny) teaches and describes a phaco emulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

U.S. Pat. No. 5,634,912 (Injev) teaches and describes an infusion sleeve having a rotating tip to allow the phaco needle to be repositioned during surgery. The top also has a single discharge port for infusing liquid during surgery.

Published U.S. Patent Application 2003/0004455 (Kadziauskas) teaches and describes a bi-manual phaco needle using separate emulsification and aspiration needles inserted into the eye simultaneously during surgery.

U.S. Pat. No. 6,007,555 (Devine) teaches and describes an ultrasonic needle for surgical emulsification and details the tendency of some ultrasonic phaco needles to force lens fragments away from the needle's aspiration port.

U.S. Pat. Nos. 6,299,591; 6,159,175; 5,743,871; 5,741,226; and 5,725,495 (Banko) all teach and describe a phacoemulsification handpiece, sleeve and tip, with the sleeve having permanently fixed exterior and/or internal baffles thereon to direct the flow of irrigation fluid away from the needle's aspiration port. The external baffles effectively increase the diameter of the sleeve while the internal baffles are relatively difficult or expensive to manufacture as compared to an extruded sleeve.

U.S. Pat. No. 7,601,135 (Akahoshi) teaches and describes a multi-port infusion sleeve with ports formed on the curved portion of the sleeve proximate the end thereof.

U.S. Pat. No. 7,601,136 (Akahoshi) teaches and describes an infusion sleeve with ports formed on the curved portion of the sleeve proximate the end thereof.

The need exists for an improved infusion sleeve which allows for a greater volume of liquid to be infused into the eye while avoiding the problems described in the prior art with respect to pushing lens and cortical material away from the aspiration port or damaging delicate eye tissue impacted by such direct flow due to increased pressure, turbulence and the like.

The need also exists for such improved infusion sleeves to incorporate a flow-directing expedient that does not extend above the surface of the sleeve during insertion and removal of the phaco needle through the incision.

The need also exists for such improved infusion sleeves to be simple in construction, efficient in operation and economical to manufacture.

SUMMARY OF THE INVENTION

In one form, the invention is directed to a phacoemulsification irrigation sleeve having a body configured to operatively connect to a phacoemulsification needle. The body has proximal and distal ends and defines a passageway for liquid. A first irrigation port is provided on the body between the proximal and distal ends of the body through which fluid in the passageway can flow. The body is slit to define a first flap. The first flap is configured to swing away from the first irrigation port in response to pressure of fluid flowing in the passageway, to thereby reduce resistance of fluid flow through the first irrigation port. The first flap is configured so that the first flap, when swinging away from the first irrigation port, is oriented to direct fluid flowing through the first irrigation port in a direction from the proximal end of the body toward the distal end of the body.

In one form, the body is slit so that a living hinge is formed that allows the first flap to swing towards and away from the first irrigation port.

In one form, the body is slit to define a "U" shape that opens towards the proximal end of the body.

In one form, the body is slit to define a horseshoe shape that opens towards the proximal end of the body.

In one form, the first flap has one of a square, rectangular, and triangular shape.

In one form, the phacoemulsification sleeve further includes at least a second irrigation port and at least a second flap substantially the same as the first irrigation port and first flap, respectively.

In one form, the phacoemulsification irrigation sleeve is provided in combination with a phacoemulsification needle.

In one form, the phacoemulsification needle has a hub. A section of the body surrounds the hub with the sleeve operatively connected to the phacoemulsification needle.

In one form, the phacoemulsification needle extends through the body to past the distal end of the body and terminates at an aspiration port.

In one form, the first flap is configured to be placed in a closed position wherein the first flap blocks the first irrigation port.

In one form, the invention is directed to a method of performing phacoemulsification. The method includes the steps of: obtaining the phacoemulsification irrigation sleeve and phacoemulsification needle as described above; and directing infusion liquid into the passageway and into the first irrigation port to thereby cause the first flap to: a) swing away from the first irrigation port; and b) direct the fluid flowing through the first irrigation port in the direction from the proximal end of the body toward the distal end of the body.

In one form, the step of causing the first flap to swing away from the first irrigation port involves causing the first flap to swing from a closed position wherein the first flap blocks the first irrigation port.

In one form, the method of performing phacoemulsification further includes the step of passing cortical and lens material into the phacoemulsification needle.

In one form, the phacoemulsification needle extends through the body to past the distal end of the body and terminates at an aspiration port. The step of passing cortical and lens material into the phacoemulsification needle involves passing cortical and lens material into the aspiration port.

In one form, the method of performing phacoemulsification further includes the step of stopping the infusion of liquid into the passageway, and thereby causing the first flap to swing back towards the first irrigation port to block the first irrigation port.

BRIEF DESCRIPTION OF THE DRAWINGS

These and further aspects of the present invention will become apparent upon consideration of the accompanying drawing figures in which:

FIG. 13 is a schematic representation of a modified form of sleeve, according to the present invention, in combination with a needle to which the sleeve is operatively connected, and having flaps with the general configuration as shown in FIGS. 8-10, but swinging in a different manner;

FIG. 14 is a schematic representation of a sleeve as in FIG. 13 and identifying a slit used to form one of the flaps;

FIG. 15 is a view as in FIG. 14 wherein the depicted slit forms a flap having a configuration different from that in FIGS. 13 and 14;

FIG. 16 is a view as in FIGS. 14 and 15 and schematically identifying slits that swing in the manner in FIGS. 8-10 but having a different configuration; and FIG. 17 is a view of a sleeve as in FIGS. 8-10 with a modified form of slit and as shown schematically in FIGS. 13-15.

DETAILED DESCRIPTION OF THE PREFERRED EMBODIMENT

Figure 1:
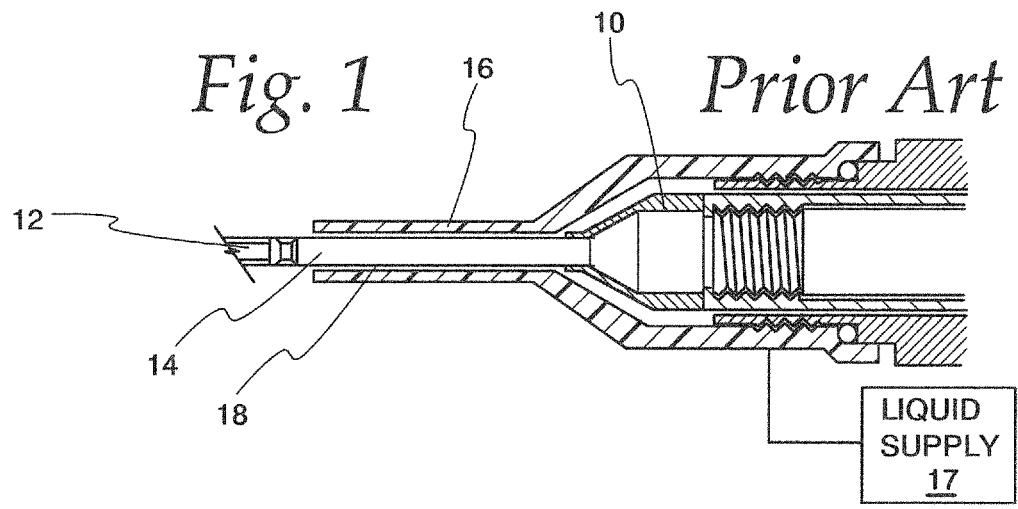
FIG. 1 is a first prior art illustration of a prior art irrigation sleeve.

Referring now to FIG. 1, the numeral 10 indicates generally a partial sectional view of a prior art phacoemulsification hand piece having a needle 12 defining a hollow internal chamber 14 through which irrigation liquid and emulsified particles of a lens are aspirated from the capsular bag. As seen in FIG. 1, an irrigating sleeve 16 is mounted to hand piece 10, from which needle 12 protrudes. Sleeve 16 communications with an irrigation liquid supply 17 within handpiece 10 and provides irrigating liquid to the capsular bag through an annular channel 18 formed between needle 12 and sleeve 16.

Figure 2:
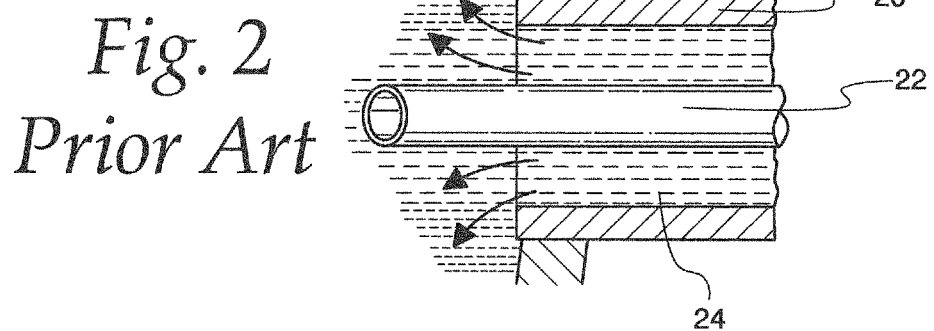
FIG. 2 is a second illustration of a prior art irrigation sleeve.

Referring now to FIG. 2, an enlarged partial sectional view of a second prior art phacoemulsification apparatus is shown having a sleeve 20 surrounding a hollow needle 22 and defining therebetween an annular channel 24 as a conduit for irrigating liquid.

Both FIG. 1 and FIG. 2 show a prior art apparatus with the flow of irrigating liquid directed annularly about the periphery of the hollow phaco needle.

Figure 3:
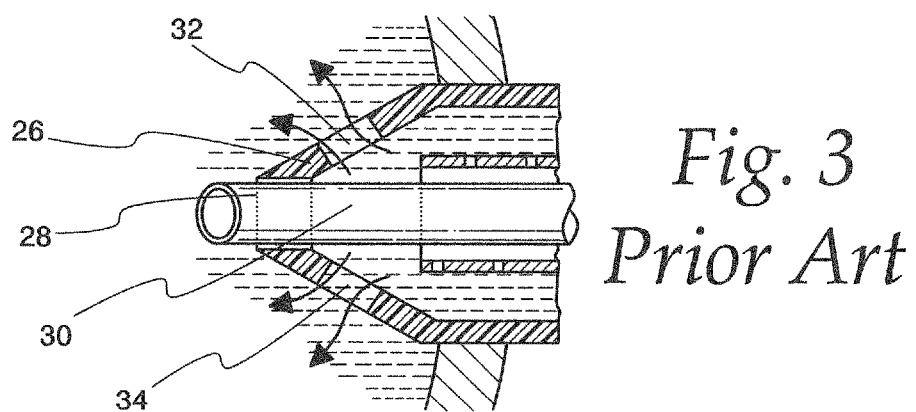
FIG. 3 is a third illustration of a prior art irrigation sleeve.

Referring now to FIG. 3, a partial sectional view of a second embodiment of the apparatus of FIG. 2 is shown where the infusion sleeve 26 tapers to form an opening 28 through which needle 30 extends. A pair of infusion ports 32, 34 is formed in the angled side walls of sleeve 26 to form a pathway for infusing liquid.

The embodiments shown in FIGS. 2 and 3 are taken from U.S. Pat. No. 5,084,009 and, as discussed above, it appears that ports 32, 34 are formed along the flattened portion of sleeve 26 and are the only infusion ports present.

Figure 4:
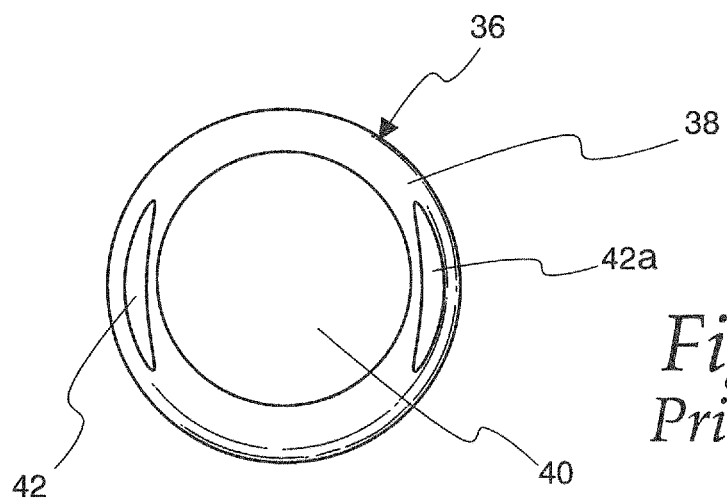
FIG. 4 is an end view of a prior art irrigation sleeve having two circular and bilaterally opposed discharge ports.
Figure 5:
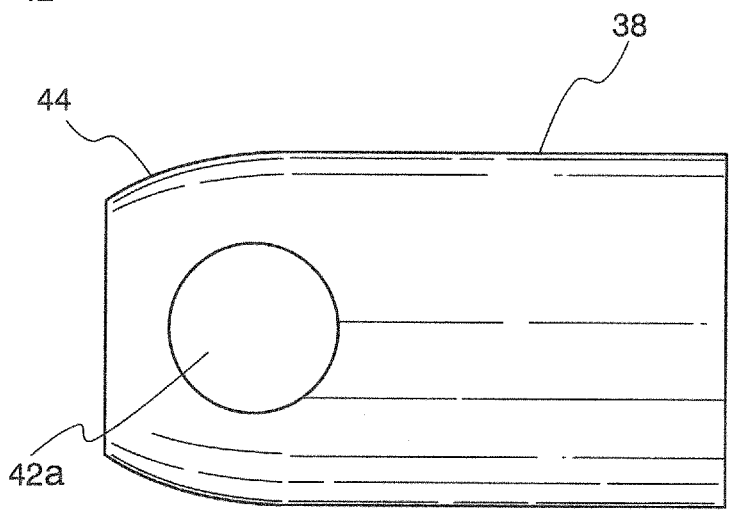
FIG. 5 is a lateral view of a portion of the sleeve shown in FIG. 4.
Figure 6:
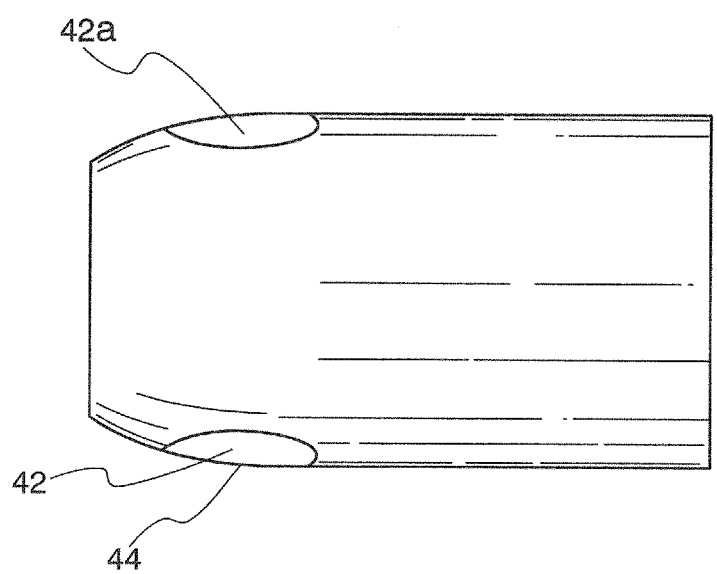
FIG. 6 is a top view of a portion of the sleeve shown in FIG. 4.

FIGS. 4-6 demonstrate a prior art phaco infusion sleeve. For purposes of clarity, only the tip portion of each such sleeve will be shown, it being understood that the sleeve is fitted coaxial to a phaco needle which extends outward from the sleeve.

FIG. 4 is an end view of a known prior art infusion sleeve 36 having an outer sleeve wall 38, a central passage 40 to accommodate the phaco needle, and a pair of diametrically opposed infusion ports 42, 42a. This is the present arrangement on a currently available infusion sleeve.

FIG. 5 is a lateral side view of the sleeve tip shown in FIG. 4, demonstrating that the infusion ports 42, 42a are circular in shape. FIG. 6 is a top view of the tip of FIG. 4, again demonstrating the diametrically opposed positions of infusion ports 42, 42a are positioned on taper 44.

Figure 7:
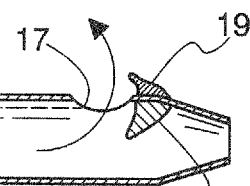
FIG. 7 is a detail view of a prior art sleeve showing interior and exterior baffles.

Referring to FIG. 7, detail of a prior art phaco sleeve is shown, corresponding to FIG. 3G of U.S. Pat. No. 6,299,591. Using the numerals in the original drawing, a phaco sleeve is shown having an irrigation port 17 through which irrigating liquid passes. Also seen in FIG. 7 are baffles 19, shown formed on both the interior and exterior of the sleeve. According to the patentee, baffles 19 redirect the flow of irrigating liquid in the direction of the arrow which, in this case, is a direction away from the aspiration port formed at the distal end of the phaco needle (not shown in this illustration). It is apparent that the exterior baffle 19 effectively increases the diameter of the sleeve and must be compressed, bent, or otherwise distended to fit through a typical incision made for phaco purposes.

Figure 8:
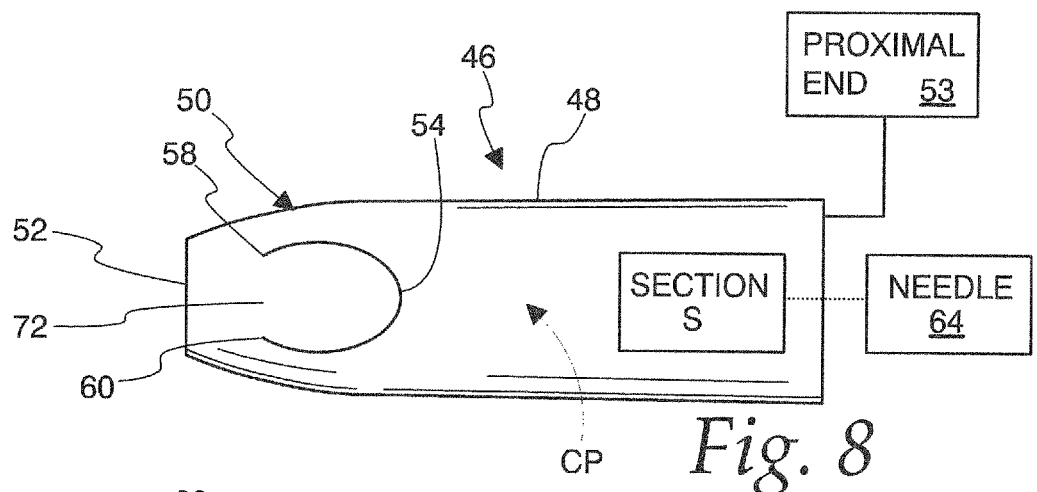
FIG. 8 is a lateral view of a sleeve embodying the present invention and having flaps that swing to control fluid flow through ports.
Figure 9:
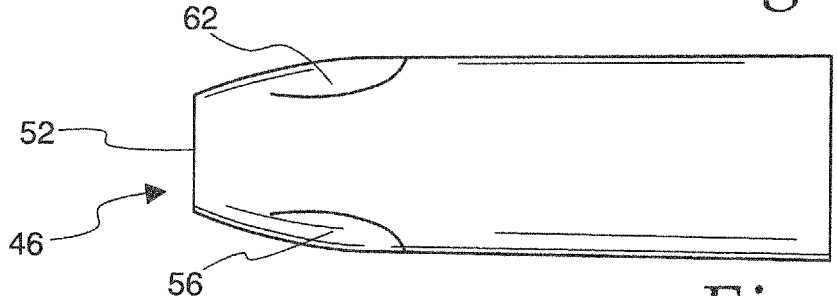
FIG. 9 is a top view of the sleeve of FIG. 8.
Figure 10:
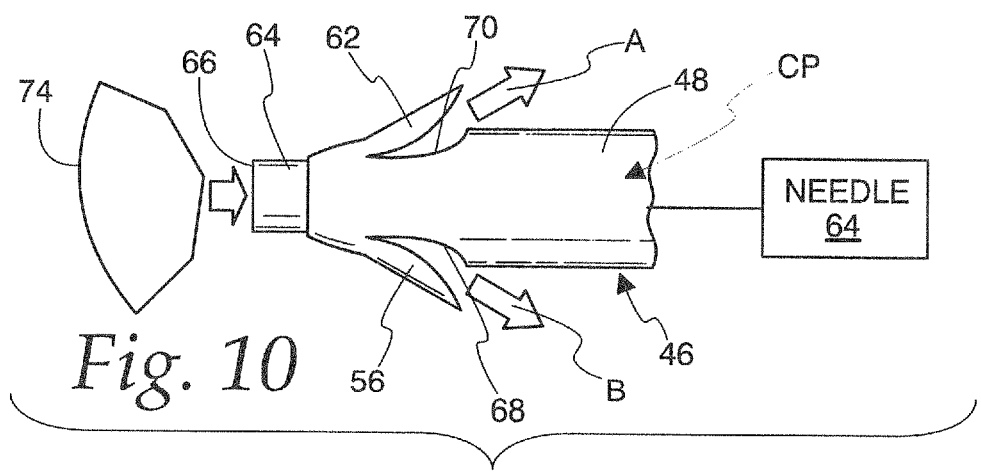
FIG. 10 is a view of the sleeve of FIG. 9 with infusing liquid passing therethrough.

Referring now to FIGS. 8-10, the numeral 46 identifies a portion of a phaco sleeve having a body 48 and a tip portion 50 which tapers to a distal end 52. The body 48 has a proximal end 53 spaced from the distal end 52. Sleeve 46 is of the type having a central passageway CP for aspiration liquid flow which extends to end 52. A section S of the body 48 is shaped and dimensioned to fit around the periphery of a hollow phaco needle 64 and allow the end of the needle to extend past the end 52 as seen in FIG. 10 with the sleeve 46 operatively connected to the needle 64.

In the embodiment shown in FIGS. 8-10, a portion of sleeve 46 is cut to form a generally U-shaped or horseshoe-shaped slit 54 to form a flap 56. Slit 54 terminates at slit end points 58, 60 which, in this embodiment, are intermediate flap 56 and end 52.

Referring now to FIG. 9, sleeve 46 is shown in a top view, showing the formation of a second flap 62, formed in the same fashion as flap 56. Although flaps 56 and 62 are shown formed to be diametrically opposed to each other on sleeve 46, it should be understood that different numbers of flaps can be formed on sleeve 46 to create or modify flow patterns as desired. In like fashion, the size and positioning of flaps such as 56 can also be changed to create different flow patterns.

Referring now to FIG. 10, the operation of sleeve 46 can now be described. In FIG. 10, sleeve 46 is seen mounted concentrically to the needle 64 which, as is typical, terminates in an aspiration port 66 through which lens and cortical material are passed. Sleeve 46 fits sufficiently liquid-tightly to needle 64 to force irrigating liquid passing through sleeve 46 at flaps 56, 62 to force flaps 56, 62, initially in their closed positions of FIGS. 8 and 9, to swing outward and away from sleeve body 48, opening infusion ports 68, 70 and directing liquid passing therethrough to flow in directions A and B which, in this embodiment, are in a direction away from aspiration port 66 (i.e., in a direction from the distal end 52 toward the proximal end 53).

In the closed position for the flaps 56, 62, the flaps 56, 62 fully block the infusion ports 68, 70. In effect, as seen in FIG. 8, the portion of sleeve 46 extending between slit end points 58, 60 forms a living hinge 72 which allows flap 56 to swing away from body 48 responsive to the pressure of the flow of liquid passing through sleeve 46. It is expected that as flow increases, flaps 56, 62 will swing farther away from body 48, thus reducing the resistance to flow through irrigation ports 68, 70. Reduction of fluid flow pressure allows the flaps 56, 62 to move towards the ports 68, 70, which eventually close, at least when there is no fluid flow.

The effect on phacoemulsification created by flaps 56, 72 is seen in FIG. 10 where, when liquid is aspirated through needle port 66, particle 74 is drawn toward aspiration port 66 without being impeded or repulsed by the flow of irrigating liquid into the eye.

While the embodiment shown in FIGS. 8-10 is intended to direct liquid flow away from aspiration port 66 in one preferred manner, it should be readily understood that the manner in which slit 54 is cut can change the flow direction.

In FIGS. 13 and 14, a modified form of sleeve, corresponding to the sleeve 46, is shown schematically at 46', with other corresponding parts identified with the same number together with a "'" designation. The sleeve 46' has a body 48' with proximal and distal ends 53', 52', respectively. Flaps 56', 62' are formed in the sleeve 46' by slitting the body 48'. Exemplary flap 56' is formed by a slit 54' that terminates at slit end points 58', 60'. Slit 54' is cut to place end points 58', 60' toward the proximal end 53' of the body 48' of sleeve 46', whereby the flap 56' would open in a fashion generally oppositely to the manner shown for the flap 56 in FIG. 10. As a result, the flap 56' is oriented to direct irrigating liquid in a forward direction, generally oppositely to that indicated by the arrow A in FIG. 10, toward aspiration port 66, should such a flow pattern be deemed useful. This is in a direction from the proximal body end 53' toward the distal body end 52'.

With the flap 56' U-shaped or horseshoe-shaped, the "U" or "U" shape of the horseshoe opens toward the proximal end 53'.

A section S' on the proximal end of the tubular body 48' is configured to surround the hub H on the phacoemulsification needle 64 and for connection to a phacoemulsification handpiece HP.

Different flow patterns can also be achieved if flap 56 is formed in a different geometrical shape, such as a square, rectangle, triangle or the like. These different shapes for the exemplary flap 56' for the sleeve embodiment shown in FIGS. 13 and 14 are encompassed by the generic showing of the sleeve 46'' in FIG. 15 with elements 48'', 52'', 53'', 54'', 58'', 60'' corresponding to like-numbered elements in FIGS. 13 and 14 but distinguished by a "''" designation.

FIG. 16 is intended to generically encompass a sleeve 46''' with the multiple different slit configurations that produce different flap shapes that open in the same manner as the flaps 56, 62 in FIGS. 8-10 open to change the effective size and shape of an irrigation port on the sleeve 46'''. The elements 48''', 52''', 53''', 54''', 58''', 60''' correspond to like-numbered elements in FIGS. 8-10 and 13-15 but are distinguished by a "'''" designation.

Figure 11:
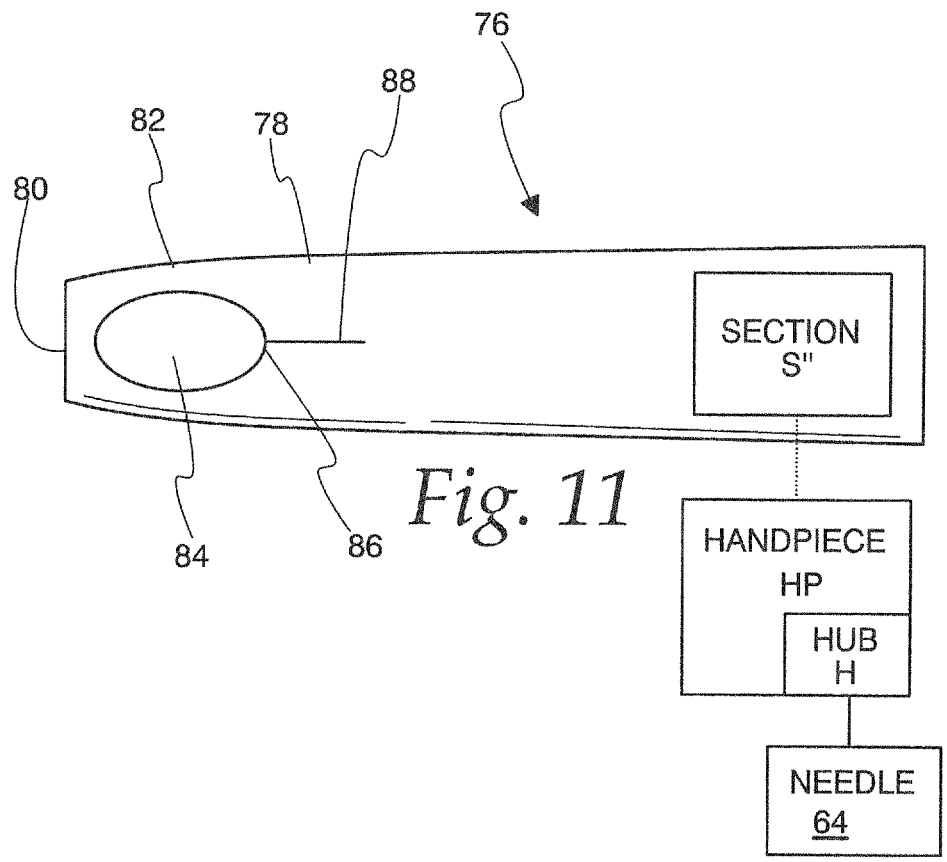
FIG. 11 is a lateral view of a sleeve embodying an embodiment of the present invention.

Referring now to FIG. 11, a phaco sleeve 76 is shown having a tip 78 terminating at an open sleeve end 80. A curved or tapered shoulder 82 extends from end 80. The depiction of sleeve 76 is for illustrative purposes, understanding that such sleeves are available in a number of different sizes and configurations.

A lateral infusion port 84 is shown on sleeve 76 as described generally above. The depiction of port 84 is illustrative only, recognizing the number of varied sizes and shapes of such ports known in the prior art. At point 86 of port 84's perimeter, a slit 88 is formed extending laterally along and through sleeve 86, beginning at and communication with port 84. In other words, port 84 is an opening extending through sleeve 76, and slit 88 likewise extends through sleeve 76 and connects with port 84.

FIG. 11 represents sleeve 76 in a first state under normal flow conditions with no occlusions of either the sleeve or the needle's aspiration port. Under such circumstances, slit 88 remains closed or undistended and little or no infusion liquid passes therethrough.

Figure 12:
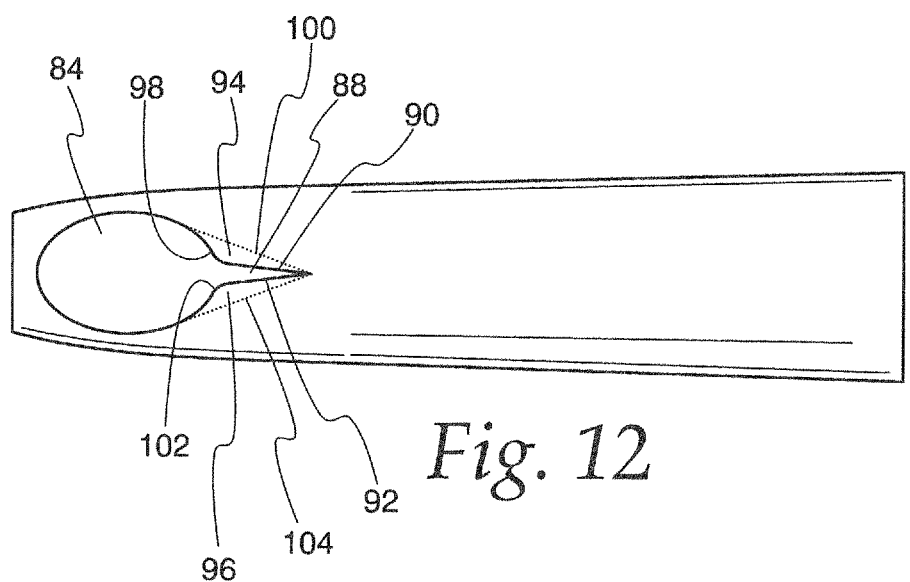
FIG. 12 is a lateral view of the sleeve of FIG. 11 showing the discharge port distended to allow increased liquid flow.

Referring now to FIG. 12, port 84 is shown as it would appear when occlusion is taking place and with the sleeve 48 in a second state. Slit edges 90, 92 have been pushed or folded outward by the force of the infusion liquid flow, forming flaps 94, 96. In this illustration, flap 94 comprises a generally triangular flap defined by slit edge 90, contiguous port rim segment 98 and "fold line" 100. Similarly, flap 96 is defined by slit edge 92, contiguous port rim portion 102 and "fold line" 104.

It should be apparent that the shape and size of flaps 94, 96 will vary with the shape and size of port 84 and the length of slit 88. All of these parameters can be selected to result in a sleeve port that will allow a determinable change in flow characteristics to meet the demands of a particular sleeve configuration or phaco needle apparatus. In any such configuration the distension or "folding out" of flaps 94, 96 creates a larger cross-section available for infusion liquid flow when occlusion or other changes in flow occur. When the flow returns to normal, flaps 94, 96 return to their "closed" position and port 84 returns to its original configuration and size.

A section S'' on the proximal end of the tubular body is configured to surround the hub H on the phacoemulsification needle 64 and for connection to the phacoemulsification handpiece HP.

One specific form of the flap 56', depicted schematically in FIGS. 13 and 14, is shown in FIG. 17 on a portion of the body 48' of the sleeve 46'. The flap 56' is formed by the slit 54' that has an overall "U" shape opening toward the proximal end 53' of the body 48'. The "U" shape of the slit 54' is defined by a curved base portion B and spaced legs L1, L2 that project from the base portion B towards the proximal body end 53'.

The legs L1, L2 have the same shape and are curved to cooperatively approximate a portion of an oval shape, with a major axis extending parallel to the length of the sleeve 46', that terminates at points A and B. From points A and B, the slit 54' projects in straight lines SL1, SL2 to the end points 58', 60', respectively. The straight lines SL1, SL2 diverge where they project from the points A, B.

With this slit configuration, depending upon the nature of the body material and fluid pressure: a) the entire length of the flap 56' between the base B and end points 58', 60' may swing about a first live hinge LH1, defined between the spaced end points 58', 60'; b) the length of the flap 56' between the base B and points A, B may swing about a second live hinge LH2, defined between the points A, B; or c) the flap 56' may swing in stages—initially about the second live hinge LH2 and subsequently about the first live hinge LH1.

The flaps 56', 62' may have the same or a different configuration. The flaps 56', 62' may be at diametrically opposite locations or spaced in a different circumferential relationship. Use of one flap 56', 62' or more than two flaps 56', 62' are contemplated.

The foregoing disclosure of specific embodiments is intended to be illustrative of the broad concepts comprehended by the invention.

The invention claimed is:

1. A phacoemulsification irrigation sleeve comprising:
    a body configured to operatively connect to a phacoemulsification needle, the body having proximal and distal ends and defining a passageway for liquid, a first irrigation port in the body between the proximal and distal ends of the body through which fluid in the passageway can flow, the body slit to define a "U" shape that forms a first flap, the "U" shape made up of spaced, non-straight legs having spaced ends, the legs cooperatively produce a bulged shape between the leg ends, the first flap elongate in a direction between the proximal and distal ends, the body configured to define a living hinge for the first flap, the first flap configured to swing away from the first irrigation port at the living hinge in response to pressure of fluid flowing in the passageway to thereby reduce resistance of fluid flow through the first irrigation port, the first flap configured so that the first flap, when swinging away from the first irrigation port, is oriented to direct fluid flowing through the first irrigation port in a direction from the proximal end of the body toward the distal end of the body.

2. The phacoemulsification irrigation sleeve according to claim 1 wherein the body is slit to define the living hinge that allows the first flap to swing towards and away from the first irrigation port.

3. The phacoemulsification irrigation sleeve according to claim 1 wherein the "U" shape opens towards the proximal end of the body.

4. The phacoemulsification irrigation sleeve according to claim 1 wherein the phacoemulsification sleeve further comprises at least a second irrigation port and at least a second flap substantially the same as the first irrigation port and first flap, respectively.

5. The phacoemulsification irrigation sleeve according to claim 1 wherein the first flap is configured to be placed in a closed position wherein the first flap blocks the first irrigation port.

6. The phacoemulsification irrigation sleeve according to claim 1 in combination with a phacoemulsification needle.

7. The phacoemulsification irrigation sleeve according to claim 6 wherein the phacoemulsification needle has a hub and a section of the body surrounds the hub with the sleeve operatively connected to the phacoemulsification needle.

8. The phacoemulsification irrigation sleeve according to claim 6 wherein the phacoemulsification needle extends through the body to past the distal end of the body and terminates at an aspiration port.

9. A method of performing phacoemulsification, the method comprising the steps of:

obtaining the phacoemulsification irrigation sleeve and phacoemulsification needle of claim 6; and directing infusion liquid into the passageway and into the first irrigation port and thereby causing the first flap to: a) swing away from the first irrigation port; and b) direct the fluid flowing through the first irrigation port in the direction from the proximal end of the body toward the distal end of the body.

10. The method of performing phacoemulsification according to claim 9 wherein the step of causing the first flap to swing away from the first irrigation port comprises causing the first flap to swing from a closed position wherein the first flap blocks the first irrigation port.

11. The method of performing phacoemulsification according to claim 9 further comprising the step of passing cortical and lens material into the phacoemulsification needle.

12. The method of performing phacoemulsification according to claim 11 wherein the phacoemulsification needle extends through the body to past the distal end of the body and terminates at an aspiration port, and the step of passing cortical and lens material into the phacoemulsification needle comprises passing cortical and lens material into the aspiration port.

13. The method of performing phacoemulsification according to claim 9 further comprising the step of stopping the infusion of liquid into the passageway and thereby causing the first flap to swing back towards the first irrigation port to block the first irrigation port.

14. A phacoemulsification irrigation sleeve comprising:

a body configured to operatively connect to a phacoemulsification needle, the body having proximal and distal ends and defining a passageway for liquid, a first irrigation port in the body between the proximal and distal ends of the body through which fluid in the passageway can flow, the body slit to define a first flap, the first flap configured to swing away from the first irrigation port in response to pressure of fluid flowing in the passageway to thereby reduce resistance of fluid flow through the first irrigation port, the first flap configured so that the first flap, when swinging away from the first irrigation port, is oriented to direct fluid flowing through the first irrigation port in a direction from the proximal end of the body toward the distal end of the body, wherein the body is slit to define a horseshoe shape that opens towards the proximal end of the body.

15. A phacoemulsification irrigation sleeve comprising:

a body configured to operatively connect to a phacoemulsification needle, the body having proximal and distal ends and defining a passageway for liquid, a first irrigation port in the body between the proximal and distal ends of the body through which fluid in the passageway can flow, the body slit to define a first flap, the first flap elongate in a direction between the proximal and distal ends, the body configured to define a first living hinge for the first flap, a part of the first flap configured to swing away from the first irrigation port at the first living hinge in response to pressure of fluid flowing in the passageway to thereby reduce resistance of fluid flow through the first irrigation port, the first flap configured so that the part of the first flap, when swinging away from the first irrigation port, is oriented to direct fluid flowing through the first irrigation port in a direction from the proximal end of the body toward the distal end of the body, wherein the first living hinge extends between spaced points, wherein the body is configured to define a second living hinge for the first flap spaced from the first living hinge.

16. The phacoemulsification irrigation sleeve according to claim 15 wherein the first flap has one of a rectangular and triangular shape.

* * * * *